United States Patent [19]

Gramm

[11] 4,412,957

[45] Nov. 1, 1983

[54] PROCESS FOR PREPARING DIALKYL PROPANEDIIMIDATE DIHYDROHALIDES

[75] Inventor: Jeffrey S. Gramm, Wilmington, Del.

[73] Assignee: E. I. Du Pont de Nemours & Co., Wilmington, Del.

[21] Appl. No.: 388,625

[22] Filed: Jun. 15, 1982

[51] Int. Cl.$^3$ .......................................... C07C 119/055
[52] U.S. Cl. .................................................. 260/453.7
[58] Field of Search ...................................... 260/453.7

[56] References Cited

U.S. PATENT DOCUMENTS 3,538,139 11/1970 Hagemeyer, Jr. et al. ...... 260/453.7
4,310,740 1/1982 Adams .............................. 260/453.7

OTHER PUBLICATIONS

McElvain and Schroeder, JACS 71, 43 (1949).

Primary Examiner—Henry R. Jiles
Assistant Examiner—Robert C. Whittenbaugh

[57] ABSTRACT

An improved process for preparing a dialkyl propanediimidate dihydrohalide by reacting malononitrile, an alcohol, and hydrogen halide, wherein the improvement comprises conducting the reaction in a chlorofluorocarbon solvent.

16 Claims, No Drawings

PROCESS FOR PREPARING DIALKYL PROPANEDIIMIDATE DIHYDROHALIDES

BACKGROUND OF THE INVENTION

This invention relates to an improved process for preparing certain dialkyl propanediimidate dihydrohalides.

McElvain and Schroeder, JACS 71, 43 (1949), disclose the preparation of dimethyl and diethyl propanediimidate dihydrochloride by treating malononitrile and the corresponding alcohol with a large excess of hydrogen chloride using a chloroform-dioxane mixture and dioxane, respectively, as solvents. The process is disclosed to give high yields, but a reaction time of about 24 hours is required.

U.S. Pat. No. 4,310,740, issued on Jan. 12, 1982 to Adams, discloses an improved process for preparing a dialkyl propanediimidate dihydrohalide by reacting malononitrile, an alcohol and hydrogen halide in an alkyl acetate solvent.

Imido ester hydrohalides are well-known compounds. They are useful as chemical intermediates for other chemical compounds such as amidine hydrochlorides or as intermediates for herbicides as described in U.S. Pat. Nos. 4,287,343 and 4,229,960. Improvements in the process for preparing these imido ester hydrohalides are increasingly desirable and are constantly being sought. Furthermore, an improved process which provides greater ease of operation and shorter reaction times offers even greater attractions.

SUMMARY OF THE INVENTION

An improved process for preparing dialkyl propanediimidate dihydrohalides of the formula:

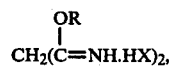

where
R=alkyl of 1 to 3 carbons, has now been found. This new process involves contacting malononitrile, an alcohol ROH, where R is as defined above, and anhydrous hydrogen halide HX, where X is chlorine or bromine, in the presence of a chlorofluorocarbon solvent having a boiling point in the range of about −45° to 100° C. at atmospheric pressure.

This new process offers a number of advantages over the best previously known process, that described in U.S. Pat. No. 4,310,740 to Adams. Not only is the rate of reaction in this new process faster than that in the Adams process, but the process can be run with greater ease due to the fact that the dialkyl propanediimidate dihydrohalide need not be isolated before use in subsequent reactions, and that the chlorofluorocarbon solvent is nonflammable, is easily recycled, and gives less corrosive reaction mixtures when mixed with hydrogen halides than does methyl acetate. Additionally, in the preferred embodiment of the Adams process, the hydrohalic acid is used in an amount sufficient to saturate the solvent. In the preferred embodiment of the new process described and claimed herein, the hydrohalic acid is used in an excess of only thirty percent over the stoichiometric amount, thus conserving material and reducing waste disposal problems.

DETAILED DESCRIPTION OF THE INVENTION

The chlorofluorocarbon solvent utilized in the improved process of this invention has a boiling point in the range of about −45° to 100° C., preferably 10° to 100° C. at atmospheric pressure. The optimal solvent to use in the process will depend on the temperature and pressure under which the reaction is run. When higher pressures are used to speed up reaction times, solvents with lower boiling points with be operable. A number of suitable chlorofluorocarbons, all methane and ethane derivatives, are commercially available. See, for example, "'Freon' Product Information," Bulletin B-2, a technical bulletin of E. I. du Pont de Nemours and Co., the disclosure of which is hereby incorporated by reference, for a listing of representative chlorofluorocarbons. Suitable chlorofluorocarbons include but are not limited to the following: chlorodifluoromethane, chloropentafluoroethane, dichlorodifluoromethane, dichlorofluoromethane, 1,1,2-trichloro-1,2,2-trifluoroethane, 1,1,2,2-tetrachloro-1,2-difluoroethane, 1,2-dichloro-1,1,2,2-tetrafluoroethane, dichlorofluoromethane and trichlorofluoromethane. Mixtures of various chlorofluorocarbons can also be used. For example, commercially available azeotropic mixtures of dichlorodifluoromethane/1,1-difluoroethane and of chlorodifluoromethane/chloropentafluoroethane colud be used as solvents in the process of this invention. The preferred chlorofluorocarbon for use as solvent in the claimed process is 1,1,2-trichloro-1,2,2-trifluoroethane, available from the Du Pont Company under the trademark Freon TF ®.

In the process of this invention, about 2 to 3 molar equivalents, based on malononitrile, of alcohol are used. Preferably about 2 to 2.2, and more preferably about 2.2, molar equivalents of alcohol are used. About 2 to 4 molar equivalents, also based on malononitrile, of hydrogen halide are used. Preferably about 2.5 to 4, and more preferably about 2.6, molar equivalents of hydrogen halide are used.

The malononitrile concentration in the chlorofluorocarbon solvent can vary from about 1 to 20 weight %. A concentration of about 5–15 weight % is preferred and 5–10 weight % is more preferred.

The process is preferably run at a temperature in the range of about 0° to 40° C., more preferably about 20° to 30° C. Pressure is not critical, and the reaction can be run under atmospheric pressure or higher pressure, the advantage of higher pressure being that reaction times can be shortened. The reaction is preferably run under pressure in the range of about 0 to 100 psig, more preferably about 10 to 100 psig. When X=Cl, it is, of course, practical to run the reaction under HCl pressure, and when X=Br it is practical to run the reaction under HBr pressure.

The order in which the reactants are contacted is not critical except that the malononitrile and the hydrogen halide are preferably not contacted in the absence of the alcohol. The reaction mixture should be agitated to insure that the malononitrile is throroughly dispersed in the solvent.

The process of this invention is further illustrated by the following examples, in which temperatures are in degrees centigrade and parts are by weight unless otherwise specified. These example are provided to illustrate the process of this invention and should not be deemed as limiting the scope thereof.

EXAMPLE 1

Preparation of Dimethyl Propanediimidate Dihydrochloride

A mixture of 58 parts of malononitrile, 63 parts of methanol, and 783 parts of 1,1,2-trichloro-1,2,2-trifluoroethane (Freon TF ®) was stirred in a 1-L pressure vessel while anhydrous hydrogen chloride was introduced at a pressure of 20 psig. The mixture was stirred and held at 23°-27° with cooling, and the HCl pressure was maintained at 20 psig until 83 parts of HCl were introduced (2.5 hours). HCl feed was then discontinued, and the reaction mass was stirred another 2 hours at 23°-27°. The resulting slurry was filtered, and the solid product was washed with Freon TF ® solvent and dried at room temperature to give 171 parts (96% yield based on malononitrile charged) of the title compound, which was identified by comparison with material produced as described in U.S. Pat. No. 4,310,740.

EXAMPLE 2

Preparation of Dimethyl Propanediimidate Dihydrochloride and Its Use in a Subsequent Reaction Without Isolation An important advantage of chlorofluorocarbon solvents over those previously used in processes for preparing dialkyl propanediimidate dihydrohalides, namely, the ability to use the crude reaction product in subsequent reactions with no workup, is illustrated as follows.

A 1-L pressure vessel was charged as in Example 1 and pressured to 24.5 psig with anhydrous hydrogen chloride gas. HCl was introduced as required to maintain this pressure, and the mixture was cooled and stirred at 25° until 83 parts of HCl had been added (3 hours). HCl feed was then discontinued, and the reaction mass was stirred overnight at 25°.

The entire reaction mass was then transferred gradually to a 2-L vessel containing a well-stirred mixture of 80 parts of 50% aqueous cyanamide and 500 parts of water. During this addition, the reaction mixture was held below 10° by external cooling, and 50% aqueous sodium hydroxide was added as required to hold the pH between 5 and 7. The resulting slurry was warmed to room temperature, stirred for two hours, and filtered. The solid product was washed with water and dried under a stream of nitrogen at room temperature to give 76.5 parts (56% based on malononitrile) of methyl 3-amino-3-methoxy-N-cyano-2-propenimidate. The identity of this material was established by comparison with material produced by the procedure of U.S. Pat. No. 4,235,802.

This product was of sufficient purity for conversion to 2-amino-4,6-dimethoxypyrimidine as described in U.S. Pat. No. 4,299,960.

What is claimed is:

1. An improved process for preparing a dialkyl propanediimidate dihydrohalide of the formula:

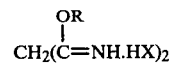

where
R is alkyl of 1 to 3 carbon atoms, and
X is chlorine or bromine, by reacting malononitrile, an alcohol ROH and anhydrous hydrogen halide HX, wherein the improvement comprises conducting the reacton in a chlorofluorocarbon solvent having a boiling point in the range of about −45° to 100° C.

2. The process of claim 1 where the solvent has a boiling point in the range of about 10° to 100° C.

3. The process of claim 2 where the solvent is 1,1,2-trichloro-1,2,2-trifluoroethane.

4. The process of any of claims 1 to 3 where the reaction is conducted under pressure of about 0 to 100 psig.

5. The process of claim 4 where the reaction is conducted under pressure of about 10 to 100 psig.

6. The process of any of claims 1 to 3 where the reaction is conducted at a temperature in the range of about 0° to 40° C.

7. The process of claim 6 where the reaction is conducted at a temperature of about 20° to 30° C.

8. The process of any of claims 1 to 3 where about 2 to 3 moles of alcohol ROH are present per mole of malononitrile.

9. The process of claim 8 where about 2.2 moles of alcohol ROH are present per mole of malononitrile.

10. The process of any of claims 1 to 3 where about 2 to 4 moles of hydrogen halide HX are present per mole of malononitrile.

11. The process of claim 10 where about 2.6 moles of hydrogen halide HX are present per mole of malononitrile.

12. The process of any of claims 1 to 3 where the concentration of the malononitrile in the chlorofluorocarbon solvent is in the range of about 1 to 20 weight percent.

13. The process of claim 12 where the concentration of the malononitrile in the chlorofluorocarbon solvent is in the range of about 5 to 10 weight percent.

14. The process of any of claims 1 to 3 where R=CH$_3$.

15. The process of any of claims 1 to 3 where X=Cl.

16. The process of claim 1 where dimethyl propanediimidate dihydrochloride is prepared by contacting malononitrile with about 2.2 moles of methanol and about 2.6 moles of anhydrous chloride, per mole of malononitrile, in 1,1,2-trichloro-1,2,2-trifluoroethane solvent, at a temperature in the range of about 20° to 30° C. and under HCl pressure of about 10 to 100 psig.

* * * * *